US010953146B2

(12) United States Patent
Klespitz

(10) Patent No.: US 10,953,146 B2
(45) Date of Patent: Mar. 23, 2021

(54) SYSTEM AND METHOD FOR FLEXIBLE CITRATE ANTICOAGULATION DURING EXTRACORPOREAL BLOOD TREATMENT USING FEED-FORWARD CONTROL

(71) Applicant: B. BRAUN AVITUM AG, Melsungen (DE)

(72) Inventor: József Klespitz, Dombóvár (HU)

(73) Assignee: B. Braun Avitum AG, Melsungen (DE)

( * ) Notice: Subject to any disclaimer, the term of this patent is extended or adjusted under 35 U.S.C. 154(b) by 1061 days.

(21) Appl. No.: 14/872,747

(22) Filed: Oct. 1, 2015

(65) Prior Publication Data

US 2016/0121035 A1    May 5, 2016

(30) Foreign Application Priority Data

Oct. 31, 2014   (EP) .................................. 14191205

(51) Int. Cl.
*A61M 1/16*      (2006.01)
*A61M 1/36*      (2006.01)

(52) U.S. Cl.
CPC ........ *A61M 1/1601* (2014.02); *A61M 1/3675* (2013.01)

(58) Field of Classification Search
CPC ..... A61M 1/1601; A61M 1/3675; A61M 1/16
(Continued)

(56) References Cited

U.S. PATENT DOCUMENTS

| 4,500,309 A | 2/1985 | Diederich |
| 2002/0107469 A1 | 8/2002 | Bolan |

(Continued)

FOREIGN PATENT DOCUMENTS

| CN | 101184517 A | 5/2008 |
| CN | 102802719 A | 11/2012 |

(Continued)

OTHER PUBLICATIONS

Chinese Office Action for Chinese Application No. 201510646690.2, dated Dec. 28, 2017, including English translation, 14 pages.

(Continued)

*Primary Examiner* — Robert Clemente
*Assistant Examiner* — Akash K Varma

(57) ABSTRACT

A system for extracorporeal blood treatment is disclosed that includes a haemofiltration device, a pump for pumping blood through the haemofiltration device, citrate means upstream to add citrate, calcium means downstream to add calcium solution, and a control configured to activate or inactivate the citrate addition means and/or the calcium addition means, wherein the control activates the citrate addition means at the beginning of blood treatment and for a first time period filters the blood with activated citrate addition means and continues to operate the citrate addition means until the end of blood treatment activates the calcium addition means after the first time period has elapsed when the total extracorporeal blood volume in the system has been filtered and citrate treated, continues to operate the calcium addition means in an active state during blood treatment to stably maintain a user-determined calcium addition rate, and continues to operate the calcium addition means in an active state after the end of blood treatment, until a second time period has elapsed after the end of treatment. A method of controlling such a system to ensure adequate calcium replenishment after citrate anticoagulation is also disclosed.

2 Claims, 2 Drawing Sheets

(58) Field of Classification Search
USPC .......................................................... 210/645
See application file for complete search history.

(56) References Cited

U.S. PATENT DOCUMENTS

| | | |
|---|---|---|
| 2004/0129638 A1 | 7/2004 | Chang et al. |
| 2004/0133145 A1* | 7/2004 | Bene .................... A61M 1/342 |
| | | 604/5.01 |
| 2005/0236330 A1 | 10/2005 | Nier |
| 2007/0066928 A1* | 3/2007 | Lannoy ................... A61M 1/16 |
| | | 604/6.07 |
| 2011/0208105 A1 | 8/2011 | Brandi |
| 2011/0264025 A1 | 10/2011 | Lannoy |
| 2012/0203159 A1 | 8/2012 | Pohlmeier |
| 2013/0165847 A1* | 6/2013 | Scarpaci ................. F04B 43/02 |
| | | 604/28 |
| 2014/0353251 A1 | 12/2014 | Kotanko et al. |

FOREIGN PATENT DOCUMENTS

| | | |
|---|---|---|
| DE | 19654746 | 7/1998 |
| EP | 2194384 | 6/2010 |
| WO | 2007038347 | 4/2007 |
| WO | 2007101064 | 9/2007 |
| WO | 2009026603 | 3/2009 |
| WO | 2010148194 | 12/2010 |

OTHER PUBLICATIONS

European Search Report dated Apr. 22, 2015 in European Application No. 14191205.5.

* cited by examiner

SYSTEM AND METHOD FOR FLEXIBLE CITRATE ANTICOAGULATION DURING EXTRACORPOREAL BLOOD TREATMENT USING FEED-FORWARD CONTROL

CROSS REFERENCE TO RELATED APPLICATIONS

This application claims priority to European application EP 14191205.5 filed Oct. 31, 2014, the contents of such application being incorporated by reference herein.

FIELD OF THE INVENTION

The present invention concerns a system and a method for flexible citrate anticoagulation during extracorporeal blood treatment using feed-forward control.

BACKGROUND OF THE INVENTION

During extracorporeal blood treatment, e.g. haemodialysis, anticoagulation is necessary to prevent thrombosis and the clotting of system in the haemodialysis machine, especially blood clotting, clotting of its filters, tubing and/or dialyzer. One possible anticoagulation method is citrate-calcium anticoagulation. This method is particularly useful in cases, in which systemic heparin anticoagulation is contraindicated. During citrate-calcium anticoagulation, citrate is added to blood in the arterial branch, which means before/upstream the dialyzer of a system for extracorporeal blood treatment e.g. of a haemodialysis machine. The added citrate prevents coagulation of blood by binding ionized calcium present in the extracorporeal blood flow within the tubing/filter of the extracorporeal blood treatment machine. As the citrate-treated blood reaches the haemodialyzer (filter), the citrate and with it the bound calcium is removed from the extracorporeal blood flow. To ensure adequate calcium homeostasis of a treated patient, the removed calcium needs to be replenished in the extracorporeal blood flow before the treated blood is returned to the patient. Hence, calcium solution is added to blood in the venous branch, which means after/downstream the dialyzer of the haemodialysis machine. The amount of citrate necessary for anticoagulation effect and the amount of calcium necessary for replacement are defined by the doctors or skilled users, who order the blood treatment (e.g. based on hospital protocol and the specific requirements of an individual patient).

DESCRIPTION OF THE RELATED ART

Several methods of citrate anticoagulation dialysis are known from the state of the art. For example, an anticoagulation strategy, in which calcium is replaced with the help of dialysate instead of calcium solution that is added to the venous branch of the haemodialysis machine, is disclosed in WO2010/148194. However, with this system it is difficult to directly control the rate of calcium addition. Hence, direct addition of calcium solution to the venous branch of the haemodialysis machine calcium addition rate is preferred, as in this case the calcium addition rate is directly amenable to immediate manipulation and not affected e.g. by diffusion of ions through the dialysate.

Furthermore, several systems and methods are known from the state of the art for controlling blood calcium levels during extracorporeal blood treatment. These conventional systems and methods use classic feed-back control loops employing a variety of sensors to monitor current blood calcium levels and adjust the citrate and calcium addition rates accordingly. The major drawbacks associated with this approach are firstly, that even advanced and, hence, costly sensors capture true calcium concentrations in a patients blood relatively inaccurately due the complexity of human calcium metabolism (free ionized calcium and calcium bound to proteins etc.) and secondly, that such automated feedback mechanisms offer hardly any flexibility to a user, such as a doctor, to adapt the settings of the haemodialysis machine even during treatment to the specific and individual requirements of each patient.

For example, WO2007/038347 discloses a system for the automated control of the electrolyte levels of a patient during haemodialysis with the help of an electrolyte sensor, a fluid loss sensor and a sensor measuring blood flow through the haemofilter. Information obtained by these sensors is used to control the addition rates of citrate and calcium solution to the blood of a patient. Due to the necessity for a plurality of sensors, this system is rather complicated and expensive to manufacture and sophisticated control algorithms are needed to ensure a correct integration of several streams of information from several sensors. This makes the whole system less user friendly in its use and increases the susceptibility of the system to user error.

Similarly from WO 2009/026603 another device for citrate anticoagulation is known, which uses a calcium sensor to monitor blood calcium levels and uses feed-back control to adjust citrate and calcium solution addition rates to maintain blood calcium levels at a certain predetermined calcium concentration.

The system of WO2007/101064A1 aims to control the electrolyte balance in the blood of a patient with the help of Raman spectrometers. These spectrometers further increase heavily the manufacturing cost of the haemodialysis system.

The method of US2012/0203159A1 similarly aims to maintain specific calcium concentrations in the blood of a patient via a feed-back mechanism involving a sensor. Furthermore, specific formulae are given to calculate possible setting ranges for calcium values.

In all of the devices known from the state of the art mentioned above, elaborate equipment in the form of sensors and complex calculating and control algorithms is required for a fully automated control of calcium levels in the blood of a patient, wherein blood calcium levels are stably maintained within a pre-determined range. This structural complexity increases the manufacturing cost of such devices and makes these devices less user-friendly in their operation.

Furthermore, such conventional methods for citrate-coagulation allow for very little or no flexibility to adjust calcium dosages during blood treatment. In addition to that, the human calcium metabolism is a very complex system. Nearly every cell of the body contains calcium and these ions have high mobility. Further complexity is added to this situation, as calcium in the blood can be present in a free ionized form as well as bound to proteins. Of these two species, only free ionized calcium is responsible for coagulation. However, as free ionized calcium is removed from the blood stream, protein bound calcium ions are released from the proteins. This inherent complexity makes it very hard to control calcium metabolism during extracorporeal blood treatment using external sources such as sensors. Especially in times of the rise of personalized medicine, there is a need for increased flexibility in treatment parameters, allowing doctors to constantly adjust treatment parameters (e.g. calcium concentration in the blood) based on their experience, a knowledge practicable during the course of treatment. This allows doctors to tailor treatment parameters to the specific requirements of individual patients as well as flexibly respond to emergencies during treatment.

SUMMARY OF THE INVENTION

An object of the present invention is to provide a system for extracorporeal blood treatment as well as a method of controlling such a system for extracorporeal blood treatment that offers increased flexibility in the setting of parameters during blood treatment, while ensuring that the correct amount of calcium is replaced in the blood of a patient (i.e. only as much calcium as has been removed during filtration), reducing the manufacturing costs of the system for extracorporeal blood treatment and facilitating the operation of the system for extracorporeal blood treatment.

This object is achieved by the system for extracorporeal blood treatment according to the independent claim.

The gist of the invention lies in using some kind of a feed-forward control mechanism to determine time periods of citrate addition and calcium addition to the blood of a patient, respectively. At the beginning of extracorporeal blood treatment, citrate is added to the blood. This is followed by a first time period until citrate is being added and the total extracorporeal blood volume is filtered. Thus, this first time period corresponds to the time taken for the system to run blood once through the entire extracorporeal circuit for extracorporeal blood treatment. After the total extracorporeal blood volume has been cleared (i.e. the first time period has elapsed), the addition of calcium at a user-defined rate commences, while citrate is still being administered and actual blood treatment, e.g. dialysis, is in operation. During the period of treatment, which may run for a given time, the user/doctor can flexibly adjust the rates of calcium and citrate addition according to her or his experience and knowledge. At the end of actual blood treatment, the addition of citrate is stopped (anticoagulation is not further required) but the addition of calcium continues for a second time period. This second time period corresponds to the time taken for the system to run blood through the entire extracorporeal circuit for extracorporeal blood treatment. Hence, if the blood flow rate has not been altered during the course of the treatment, the second time period is equal to the first time period. Based on information on the volume of the extracorporeal circuit and the flow rate of blood through the haemodialyzer, the length of the second time period can be determined. The setting of the lengths of the first and second time periods during which only citrate addition or only calcium addition occur provides a temporal control mechanism which obliterates the need for complicated sensors used to directly monitor and set calcium concentrations. Furthermore, because the replenishment of calcium during the second time period ensures that the amount of calcium removed from the blood during the treatment is replaced, a doctor can flexibly adjust treatment parameters during actual blood treatment. In a nutshell, in accordance with FIG. 2, at the beginning the extracorporeal blood is treated with citrate and for a first time period this (continuously) citrate-treated blood (calcium addition is still stopped) is filtered through the semipermeable membrane. Subsequently (start of regular treatment period), some time is spent in blood treatment, e.g. dialysis, at user defined settings (which can be adjusted during treatment). Meanwhile, the citrate bound calcium ions are filtered from the blood through the semipermeable membrane (haemofilter or dialyzer), which ions are (continuously) replaced by calcium addition which has been started at the end of the first time period. After treatment (end of regular filter treatment period) calcium addition is continued for a second time period (wherein citrate addition has been stopped at the end of the regular filter treatment period), to replenish blood calcium level in the treated blood before it is returned to the body of the patient. Both the first and the second time periods are the time periods required for the system to run blood once through the entire extracorporeal circuit. This time period corresponds with the extracorporeal volume of the system and the flow rate of blood.

A system for extracorporeal blood treatment according to aspects of the present invention comprises a haemofiltration device, means for pumping blood through the haemofiltration device (e.g. a blood pump), citrate addition means (e.g. a citrate pump or infusion line) arranged upstream of the haemofiltration device in the direction of blood flow/on the arterial branch of the system for extracorporeal blood treatment and configured to add citrate to the blood, calcium addition means (e.g. a calcium pump or infusion line) arranged downstream of the haemofiltration device in the direction of blood flow/on the venous branch of the system for extracorporeal blood treatment and configured to add calcium solution to the blood, and control means (e.g. an electronic control unit, ECU) configured to activate or inactivate (i.e. switch on and off) the citrate addition means and/or the calcium addition means and to define the addition rates for citrate addition means and/or calcium addition means according to the user defined settings. When a patient is connected to the system for extracorporeal blood treatment, the control means activates (i.e. switches on) the citrate addition means at the beginning of blood treatment. Subsequently, before calcium addition means is activated for a first time period citrate treated blood is filtered through the dialyzer, while citrate addition means remain active. This first time period corresponds to the time required for the system to run blood once through the extracorporeal circuit for extracorporeal blood treatment. This ensures that most of the ionized calcium is removed from the blood in the extracorporeal circuit while blood treatment is performed therefore blood clotting will not occur. When blood treatment is started and treatment is continued, the control means maintains the citrate addition means in an active state and additionally after the first time period has elapsed the control means activates the calcium addition means. During blood treatment a user, such as a doctor, can flexibly adjust the addition rates of calcium and citrate to maintain a user-determined calcium concentration in the blood of the patient. The rate of calcium and/or citrate addition can be repetitively varied by the doctor during blood treatment. After the end of blood treatment (i.e. after the end of the last cycle of blood treatment) the control means inactivates (i.e. switches off) the citrate addition means. However, the control means continues to operate the calcium addition means in an active state (i.e. switched on) after the end of blood treatment, until a second time period has elapsed after the end of treatment. This second time period corresponds to the time taken for the system to run blood once through the entire extracorporeal circuit for extracorporeal blood treatment. Thus, operating the calcium addition means during the second time period in an active state ensures that all calcium withdrawn from the blood during the treatment is actually replaced until the end of the second time period.

By using a feed-forward mechanism to set the length of the second time period based on the length of the first time period, the need for elaborate sensors detecting blood calcium concentrations is obviated and the manufacturing cost of the system for extracorporeal blood treatment can be reduced. Furthermore, the control over the calcium dosage and calcium concentrations in the blood during blood treatment is in the hands of the doctor, as the temporal coordination of citrate addition meanwhile blood treatment and calcium replenishment meanwhile and calcium replenishment after blood treatment ensures an adequate replacement of calcium to the blood of the patient independent of the treatment parameters (e.g. calcium or citrate addition rates) used during blood treatment.

In case the treatment is suspended for any reason (e.g. necessary intervention on the patient without blood treatment, detection of any disorder, necessity of third-part intervention, etc.) the control means inactivates (i.e. switches off) citrate addition means. Meanwhile the control means keeps calcium addition active (i.e. switched on) for the second time period. This second time period corresponds to the time taken for the system to run blood once through the entire extracorporeal circuit for extracorporeal blood treatment.

In certain cases the first time period (i.e. when only citrate addition is active) and the second time period (i.e. when only calcium addition is active) could overlap. In this cases control means keeps citrate addition means active during the first time period, while citrate treated blood is filtered through the dialyzer. At the beginning of the second time period the control means inactivates the citrate addition means, while activates the calcium addition means. In this case the first time period lasts until control means inactivates citrate addition means. The second time period corresponds to the time of the system spent in treatment. (The maximum of the second time period corresponds to the time taken for the system to run blood once through the entire extracorporeal circuit for extracorporeal blood treatment.) The volume of blood replenished with calcium ions shall be the same volume filtered by the system (as only that blood needs replenishment, where the clearance removed calcium ions during treatment).

In certain cases it is possible and it is allowed, that the above mentioned scenarios change each others.

In an advantageous embodiment of the present invention, the second time period and the first time period are set by the control means to be substantially equal to the time taken for the system to run blood once through the entire extracorporeal circuit for extracorporeal blood treatment.

In a modification of that embodiment, the control unit additionally uses information on the given flow rate of blood and time spent in treatment (i.e. active clearance) through the system for extracorporeal blood treatment to calculate the first and second time periods.

In an advantageous embodiment of the invention, the user-determined calcium addition rate is constant over the course of the blood treatment. Alternatively, the user-determined calcium addition rate is variable over the course of the blood treatment.

In another advantageous embodiment of the invention the control unit activates and/or inactivates the calcium addition means and/or the citrate addition means to maintain calcium levels in the blood (both extra- and intracorporally) at user-determined calcium concentrations.

Another aspect of the invention concerns a method of controlling a system for extracorporeal blood treatment to ensure adequate calcium replenishment after citrate anticoagulation, the method comprising the steps:

feeding blood through an extracorporeal blood circuit, preferably with a predetermined flow rate (volume/sec).

beginning the addition of citrate to the blood volume, starting with blood treatment for a first time period until the entire extracorporeal blood volume is treated effecting the addition of calcium to a blood volume after the first time period has elapsed (start of regular filtration period), maintaining citrate addition until the end of blood treatment (end of regular treatment period), at which point in time citrate addition is stopped, maintaining calcium addition during blood treatment to stably maintain a user-determined calcium addition rate, continuing the addition of calcium after the end of blood treatment (end of regular treatment period), until a second time period starting from the end of blood treatment required to add calcium to the treated extracorporeal blood volume in the system has elapsed after the end of treatment, stopping addition of calcium, returning extracorporeal blood back to the patient.

In an advantageous embodiment of that method, the first and second time periods correspond to the time taken for the system to run blood once through the entire extracorporeal circuit for extracorporeal blood treatment.

In a modification of that embodiment, the first and second time periods may be shorter than the period mentioned above.

Additionally the time lengths of the first and second time periods can be calculated taking into consideration information on the current flow rate of blood through the system for extracorporeal blood treatment during the first and second time periods and the volume of the treated blood volume (filtered blood volume).

In an embodiment of this method, information on the length of the first time period is used to determine the length of the second time period using feed-forward control.

A method according to aspects of the present invention allows that during blood treatment the citrate addition rate and the calcium addition rate to the blood volume are set to maintain calcium levels in the blood (both extra- and intracorporally) at user-determined calcium concentrations. The user-determined calcium addition rate of the calcium addition means can be constant or variable over the course of the blood treatment, the method according to aspects of the present invention offers increased flexibility to a doctor carrying out blood treatment.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
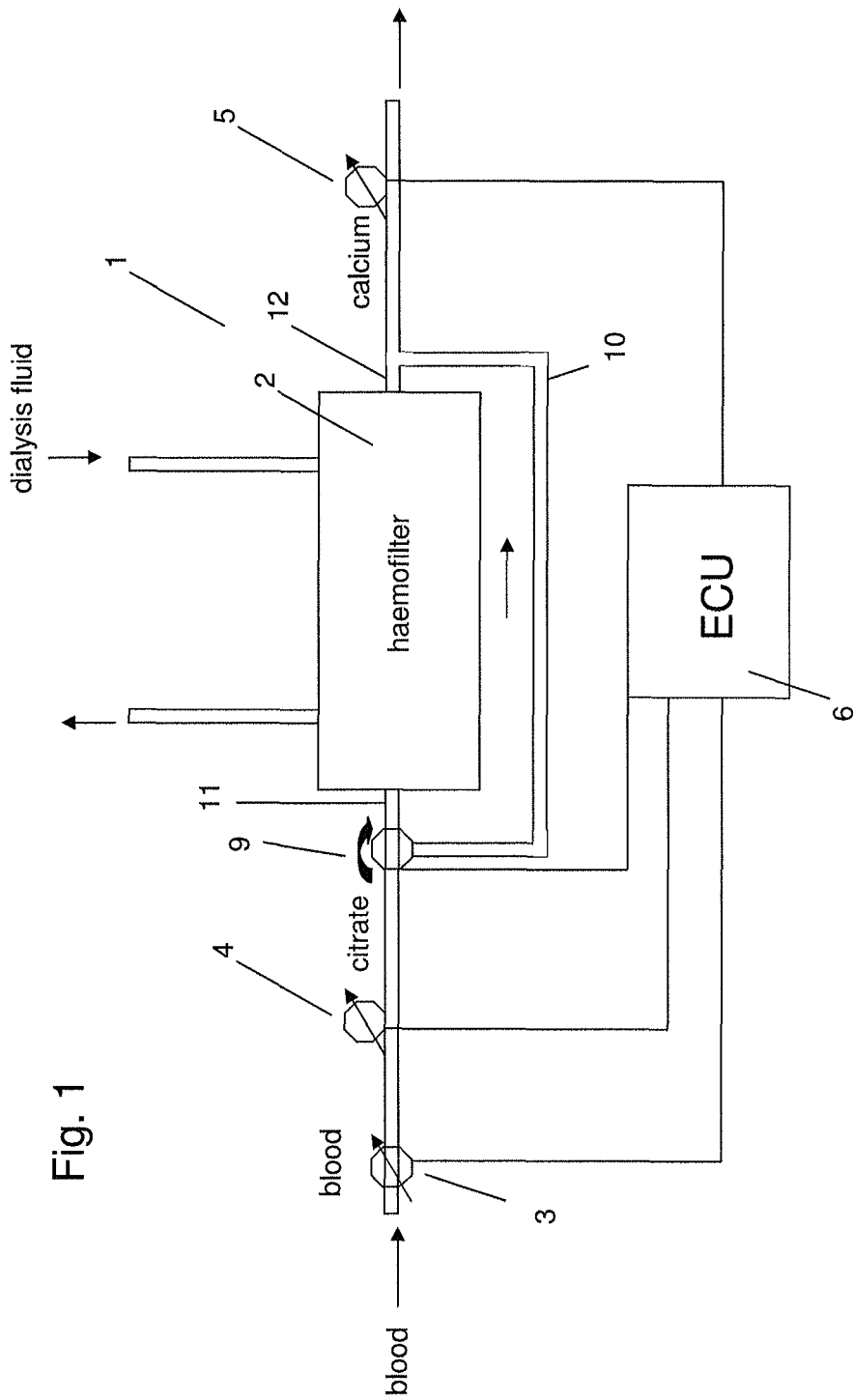
FIG. 1 shows a diagram of a system for extracorporeal blood treatment according to aspects of the present invention.

FIG. 1 shows a system for extracorporeal blood treatment 1, e.g. a haemodialysis machine, comprising a haemofilter 2, a blood pump 3 for pumping blood through the haemofilter 2, a citrate pump 4 configured to add citrate to the blood and arranged upstream of the haemofilter 2 in the direction of blood flow through the haemofilter 2, a calcium pump 5 configured to add calcium solution to the blood and arranged downstream of the haemofilter 2 in the direction of blood flow through the haemofilter 2, and an electronic control unit (ECU) 6 configured to activate or inactivate (i.e. switch on and off) the citrate pump 4 and/or the calcium pump 5. Furthermore, the haemodialysis machine comprises an inlet 11 allowing a flow of dialysis fluid into the haemofilter 2 and an outlet 12 allowing flow of dialysis fluid out of the haemofilter 2. Dialysis fluid flows through the haemofilter 2 in a direction opposing the direction of blood flow through the haemofilter 2. At the very beginning of blood treatment, the ECU 6 switches on the citrate pump 4. For a first time period until the total extracorporeal blood volume of the system has run through the circuit of the haemodialysis machine once the citrate pump 4 is kept switched on and the blood is filtered through the haemofilter 2. When the total extracorporeal blood volume has been treated, the ECU 6 switches on the calcium pump 5 with a user-defined flow while continuing to operate the citrate pump 4. This state is maintained until treatment stops for any reason. The rate of addition of calcium and/or citrate can be varied by the user or a doctor during the course of blood treatment. If the citrate treatment is stopped and the citrate pump 4 is inactive but the blood pump 3 is running, the ECU 6 maintains the calcium pump 5 in the active state/switched on. The ECU 6 may maintain the calcium pump 5 in the active state for a second time period corresponding to the time taken for the extracorporeal total blood volume of the system to run through the circuit of the haemodialysis machine 1 once. In this case, the treatment can be stopped. Alternatively, if treatment is to be continued and the citrate pump 4 is activated again by the ECU 6, the ECU 6 inactivates the calcium pump 5. Subsequently, the ECU 6 reactivates the calcium pump 5, when the total extracorporeal blood volume has been filtered. During the whole course of blood treatment, the ECU 6 does not directly exert any control on the calcium concentration in the blood. Instead, a user or a doctor defines the calcium and citrate addition rates. The ECU 6 only defines the time periods during which the citrate pump 4 and the calcium pump 5 are active/inactive.

Figure 2:
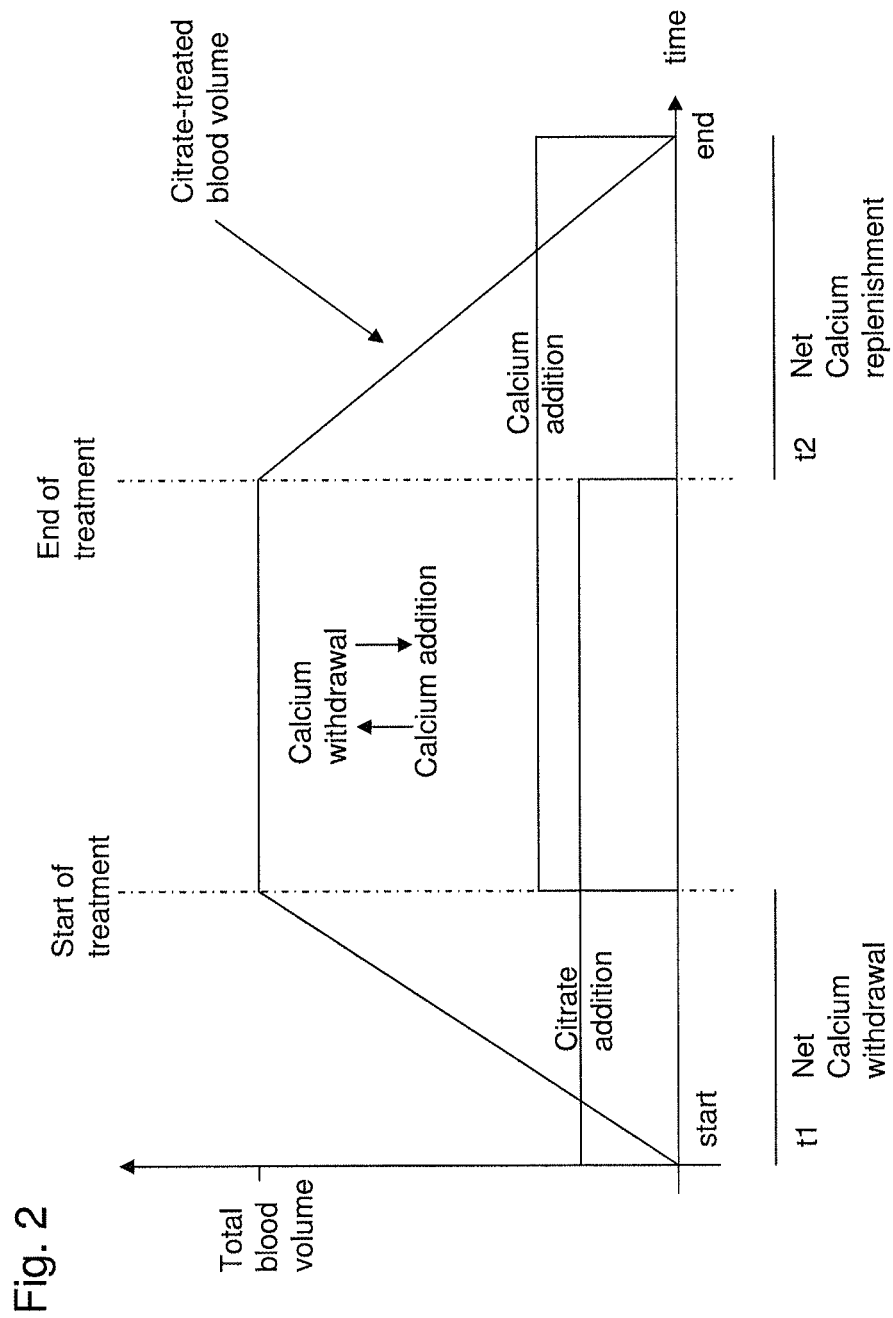
FIG. 2 shows a process diagram of a method for controlling a system for extracorporeal blood treatment to ensure adequate calcium replenishment for citrate anticoagulation.

FIG. 2 shows a process diagram of a method of controlling a system for extracorporeal blood treatment to ensure adequate calcium replenishment after citrate anticoagulation by regulating the temporal sequence (which may include overlaps) of the addition of citrate and calcium. The figure shows two correlated diagrams. Time runs on the x axis in both cases. The y axis shows the patient volumes on the upper diagram and shows extracorporeal volumes on the lower diagram. When a patient is newly connected to the system for extracorporeal blood treatment the citrate treated blood volume and the filtered blood volume are zero in the disposable kit, while the volume of citrate, calcium, and waste materials in the patients blood stand at their original level. At first citrate addition is activated, this way citrate treated blood volume and the patient citrate volume begin to increase in the disposable kit. After the treatment has been started the treated blood volume begins to increase in the disposable kit, while the citrate treated blood volume further increases. Meanwhile the patient citrate volume stops in the increase, as no further citrate is pumped back to the patient. During the therapy no more citrate burden will happen and the amount administered to the patient will be decomposed due to metabolical processes. The citrate treated blood volume and the filtered blood volume continues to increase until they separately reach the amount of total extracorporeal blood volume. Until the filtered blood volume do not reach the amount of total extracorporeal blood volume the calcium is removed from the blood without replacement, therefore the patient calcium volume decreases. After the filtered blood volume reaches the amount of extracorporeal blood volume the calcium addition starts. Thus, the filtered calcium is replaced and the patient calcium volume remains unchanged. Meanwhile the volume of waste products in the patient's blood decreases until the end of treatment. At the end of treatment citrate addition stops and after this the citrate treated blood volume and filtered blood volume will decrease in the disposable kit, while calcium addition remains active. Therefore patient calcium volume will increase and the volume of waste products in the patient's blood remains unchanged. As the times are supposed to be equal when there is calcium withdraw without replacement (t1) and when there is calcium replacement without withdraw (t2) as a result the patient calcium volume is equal to the original volume. In summary a system for extracorporeal blood treatment is provided, with:

a haemofiltration device, means for pumping blood through the haemofiltration device, citrate addition means arranged upstream of the haemofiltration device in the direction of blood flow configured to add citrate to the blood, calcium addition means arranged downstream of the haemofiltration device in the direction of blood flow configured to add calcium solution to the blood, and control means configured to activate or inactivate the citrate addition means and/or the calcium addition means, wherein the control means activates the citrate addition means at the beginning of blood treatment and for a first time period filters the blood with activated citrate addition means and continues to operate the citrate addition means until the end of blood treatment, at which point in time the citrate addition means is inactivated, the control means activates the calcium addition means after the first time period has elapsed, when the total extracorporeal blood volume in the system has been filtered and citrate treated, continues to operate the calcium addition means in an active state during blood treatment to stably maintain a user-determined calcium addition rate and continues to operate the calcium addition means in an active state after the end of blood treatment, until a second time period has elapsed after the end of treatment. Furthermore, it comprises the method of controlling such a system for extracorporeal blood treatment to ensure adequate calcium replenishment after citrate anticoagulation.

The invention claimed is:

1. A method for controlling a system for extracorporeal blood treatment having a hemofiltration device, a pump configured to pump blood through the hemofiltration device and an extracorporeal circuit of the system, a citrate addition means arranged upstream of the hemofiltration device in a direction of blood flow configured to add citrate to blood, a calcium addition means arranged downstream of the hemofiltration device in the direction of blood flow configured to add calcium to blood, and a control unit configured to control activation of the citrate addition means and the calcium addition means; the method comprising:

pumping, with the pump, blood from a patient through the extracorporeal circuit; activating, with the control unit, the citrate addition means at or before a beginning of a blood treatment;

determining, with the control unit, elapse of a first time period after beginning the blood treatment, the first time period equal to an amount of time required for blood to run once completely through the extracorporeal circuit;

operating continuously, with the control unit, the citrate addition means when blood treatment is running, at which time a first amount of calcium is removed from the blood;

inactivating, with the control unit, the citrate addition means when the blood treatment is stopped;

activating, with the control unit, the calcium addition means after the first time period has elapsed, wherein total extracorporeal blood volume in the system has been filtered and treated with citrate;

operating continuously, with the control unit, the calcium addition means in an active state during the blood treatment to stably maintain a user-determined calcium addition rate;

determining, with the control unit, elapse of a second time period after stopping the blood treatment, wherein:

if blood flow rate is not altered during the blood treatment, the second time period is equal to the first time period; and if blood flow rate is altered during the blood treatment, the second time period is equal to the volume of the extracorporeal circuit divided by the flow rate of blood through the hemofiltration device;

operating continuously, with the control unit, the calcium addition means after stopping the blood treatment, until the second time period has elapsed after the end of the blood treatment, at which time a second amount of calcium is added to the blood that is equal to the first amount of calcium;

inactivating, with the control unit, the calcium addition means when the second time period elapses; and returning, with the pump, blood to the patient.

2. A method for controlling a system for extracorporeal blood treatment having a hemofiltration device, a pump configured to pump blood through the hemofiltration device and an extracorporeal circuit of the system, a citrate addition means arranged upstream of the hemofiltration device in a direction of blood flow configured to add citrate to blood, a calcium addition means arranged downstream of the hemofiltration device in the direction of blood flow configured to add calcium to blood, and a control unit configured to control activation of the citrate addition means and the calcium addition means; the method comprising:

pumping, with the pump, blood from a patient through the extracorporeal circuit; activating, with the control unit, the citrate addition means at or before a beginning of a blood treatment;

determining, with the control unit, elapse of a first time period after beginning the blood treatment, the first time period equal to an amount of time required for blood to run once completely through the extracorporeal circuit;

operating continuously, with the control unit, the citrate addition means when blood treatment is running, at which time a first amount of calcium is removed from the blood;

inactivating, with the control unit, the citrate addition means when the blood treatment is stopped;

activating, with the control unit, the calcium addition means after the first time period has elapsed, wherein total extracorporeal blood volume in the system has been filtered and treated with citrate;

operating continuously, with the control unit, the calcium addition means in an active state during the blood treatment to stably maintain a user-determined calcium addition rate;

determining, with the control unit, elapse of a second time period after stopping the blood treatment, the second time period equal to the volume of the extracorporeal circuit divided by the flow rate of blood through the hemofiltration device;

operating continuously, with the control unit, the calcium addition means after stopping the blood treatment, until the second time period has elapsed after the end of the blood treatment, at which time a second amount of calcium is added to the blood that is equal to the first amount of calcium;

inactivating, with the control unit, the calcium addition means when the second time period elapses; and returning, with the pump, blood to the patient.

* * * * *